(12) United States Patent
Sako et al.

(10) Patent No.: US 6,262,294 B1
(45) Date of Patent: Jul. 17, 2001

(54) PROCESS FOR CONTINUOUSLY PRODUCING MONOMER COMPONENTS FROM AROMATIC POLYESTER

(75) Inventors: Takeshi Sako, Tsukuba; Masazumi Godo, Suwa; Seiji Ishida, Hachioji; Kunio Miura; Masayuki Tsugumi, both of Suwa, all of (JP)

(73) Assignees: Agency of Industrial Science and Technology; Shin Nippon Air Technologies Co., Ltd., both of Tokyo (JP)

( * ) Notice: Subject to any disclaimer, the term of this patent is extended or adjusted under 35 U.S.C. 154(b) by 0 days.

(21) Appl. No.: 09/504,900

(22) Filed: Feb. 16, 2000

(30) Foreign Application Priority Data

Feb. 17, 1999 (JP) .................................................. 11-038396
Jul. 29, 1999 (JP) .................................................. 11-214489

(51) Int. Cl.⁷ .................................................... C07C 67/48
(52) U.S. Cl. ............................................................. 560/78
(58) Field of Search ............................................... 560/78

(56) References Cited

U.S. PATENT DOCUMENTS 5,298,530    3/1994   Gamble et al. .
5,654,470 * 8/1997   Naujokas et al. .

FOREIGN PATENT DOCUMENTS

758640 * 2/1997 (EP) .
09249597    9/1997 (JP) .

OTHER PUBLICATIONS

Hawley's Condensed Chemical Dictionary Thirteenth Edition, pp. 360 and 765.

* cited by examiner

Primary Examiner—Ralph Gitomer
Assistant Examiner—Devesh Khare
(74) Attorney, Agent, or Firm—McDermott, Will & Emery

(57) ABSTRACT

This invention relates to a process for producing aromatic divalent carboxylic acid ester and diatomic alcohol by reacting aromatic polyester and super critical monatomic alcohol, and by the process, PET is decomposed for recovering monomer components therefrom, and thus recovered monomer components can be used as the material for reproduction of new PET.

In accordance with the present invention, there is provided a process for producing continuously monomer components from aromatic polyester, the process including the steps of: feeding continuously the above aromatic polyester and the above monatomic alcohol into a reactor while the above reactor is kept to be under the super critical condition of the above monatomic alcohol; reacting the above aromatic polyester and the above super critical monatomic alcohol and discharging the resultant reaction products, i.e., aromatic divalent carboxylic acid ester and diatomic alcohol, together with the monatomic alcohol from the reactor; and separating, from the above discharged resultant products, the above aromatic divalent carboxylic acid ester and the above diatomic alcohol and recovering them.

8 Claims, 2 Drawing Sheets

PROCESS FOR CONTINUOUSLY PRODUCING MONOMER COMPONENTS FROM AROMATIC POLYESTER

The present application claims the foreign priority of Japan 11-038396 Feb. 17, 1999 and Japan 11-21448 Jul. 29, 1999.

FIELD OF THE INVENTION

This invention relates to a process for continuously producing, from aromatic polyester, an aromatic dicarboxylic acid and ester a dihydric alcohol as the monomer components of the aromatic polyester.

BACKGROUND OF THE INVENTION

As one of typical aromatic polyesters, polyethylene terephthalate is known. The polyethylene terephthalate (PET) is used as the material of bottles containing beverages and other liquids, so-called PET bottles. Most of spent PET bottles are disposed of by incineration or landfill. However, these disposal methods are not preferable from the viewpoints of reuse of resource and environmental protection. So, it is desired to develop recycling technology for recovering spent PET bottles. Necessity for developing such technology is increased with growing consumption of PET bottles. Several methods have been developed in each of which, PET is decomposed for recovering monomer components therefrom, and thus recovered monomer components can be used for reproduction of new PET bottles.

Among these conventional methods, typical ones are listed below.

(1) Methanolysis method where solvolysis is carried out with liquid methanol;

(2) Glycolysis method where solvolysis is carried out with ethylene glycol;

(3) Ester interchange method where methyl esterification is carried out after the Glycolysis method (2); and (4) Alkali hydrolysis method where hydrolysis is carried out with alkali solution.

Further, in these days, the following two methods are proposed.

(A) Method for obtaining terephthalic acid where PET is hydrolized with super critical water; and (B) Method for recovering monomer components where super critical methanol and PET are reacted in a batch type reactor as disclosed in Japanese Patent No. 2807781.

However, the above methods have drawbacks respectively.

In the method (1) (Methanolysis method), its reaction temperature is so low of about 450 K that its reaction rate is small. Accordingly, catalysts are required to accelerate its reaction, which leads to increased cost.

In either of the method (2) (Glycolysis method) and method (3) (Ester interchange method), catalyst is required like the method (1) (Methanolysis method). Further, either of their reaction steps is complicated.

In either of method (4) (Alkali hydrolysis method) and method (A) (Method for obtaining terephthalic acid), it is difficult to purify the terephthalic acid obtained by the hydrolysis. Particularly, in the method (A) (Method for obtaining terephthalic acid), the reaction conditions are very severe. Concretely, the reaction temperature is very high (same as or higher than 450 K) and the reaction pressure is also very high (same as or higher than 30 MPa). Further, it is substantially impossible to recover perfectly the monomer components, since one resultant monomer component (ethylene glycol) is decomposed due to catalytic action, which is performed by another resultant monomer component (terephthalic acid) in the solution.

In the method (B) (Method for recovering monomer components) disclosed in Japanese Patent No. 2807781, the following process is performed. First, methanol and aromatic polyester are fed in the weight proportion of the same as or higher than 10 mol, preferably 20 to 70 mol of methanol per 1 mol of aromatic dicarboxylic acid in the aromatic polyester. Then, they are reacted under the conditions of temperature of 512.6 to 673 K, preferably 523 to 653 K and of pressure of 3 to 30 MPa, preferably 5 to 25 MPa. But this Japanese Patent does not refer to an industrial process for continuously producing monomer components. In the method of this patent, when the reaction products are recovered after cooling of the reactor, the recovered dimethyl terephthalate is precipitated due to its low solubility to the methanol, and therefore, it takes trouble to discharge this product. Additionally, since the dimethyl terephthalate, on recovering, tends to be mixed with not-yet-decomposed PET, a separation step is required to separate the not-yet-decomposed PET and the produced dimethyl terephthalate. Further, because of low level of recovering efficiency, this method is not suitable for practical use in the field of industry.

It is, therefore, the first object of the present invention is to provide a process by which monomer components can be produced continuously from the aromatic polyester with high yield as well as by which the monomer components can be recovered and separated simply under industrially advantageous conditions.

The second object of the present invention is to, in this process, discharge the large amount of reaction products from the reactor during the reaction and to increase the throughout per unit time for improved productivity. By attaining this second object, after reaction is carried out continuously for a certain period and the pressure in the reactor is reduced to the atmospheric pressure, the reaction products can be recovered not in batch operation but in continuous operation.

The third object of the present invention is to increase the purity of monomer components as products and to prevent oligomer components from remaining in the monomer components.

SUMMARY OF THE INVENTION

In accordance with the present invention, there is provided a process for continuously producing monomer components from aromatic polyester by reaction of the aromatic polyester and super critical monohydric alcohol to obtain aromatic carboxylic acid ester and diatomic alcohol, the process comprising the steps of: feeding continuously the above aromatic polyester and the above monatomic alcohol into a reactor while the above reactor is kept to be under the super critical condition of the above monatomic alcohol; reacting the above aromatic polyester and the above super critical monatomic alcohol and discharging the resultant reaction products i.e., aromatic divalent carboxylic acid ester and diatomic alcohol, together with the monatomic alcohol from the reactor; and separating, from the above discharged resultant products, the above aromatic divalent carboxylic acid ester and the above diatomic alcohol and recovering them.

In the present invention, the aromatic polyester includes not only polyethylene terephthalate (PET) but also polyethylene naphthalate (PEN) and the like. The monatomic alcohol of the present invention includes not only methanol but also ethanol and the like.

Since the reaction between the aromatic polyester and monatomic alcohol is one of typical ester exchange reactions, the components are allowed to come to certain equilibrium under the conditions of certain temperature and certain pressure. However, according to the present invention, as the reaction products together with the super critical monatomic alcohol are discharged out of the reactor, the equilibrium is shifted to the side of the reaction products. Hence, the decomposing reaction can be accelerated resulting in that the monomer components can be recovered with high yield. Further, when the reaction products are discharged together with the super critical monatomic alcohol, it is not necessary to cool the reactor after the reaction, which is different from the batch type reaction stated before. Therefore, in spite of low solubility of aromatic divalent carboxylic acid ester to the monatomic alcohol, the acid can be recovered with high yield.

On the other hand, under such super critical conditions of high temperature and high pressure, the reactor should be thick-walled and sometimes should be a pressure reactor surrounded by heat medium. Conventionally, in each reactor, there was no way to determine the boundary position formed between the super critical monatomic alcohol phase and the aromatic polyester phase. Precisely, operation was carried out continuously, while the boundary position formed-between these two phases could not be determined. Accordingly, the liquid phase might be often eliminated or introduced into a discharge line, which might, in some cases, led to shutdown of plant.

In comparison with this, by feeding the above monatomic alcohol into the above reactor with a constant flow rate and the aromatic polyester with a controlled flow rate while the above boundary position formed between these two phases is determined, the above mentioned undesirable accidents can be prevented. That is to say, the liquid phase will not be eliminated and not be introduced into the discharge line, thus, the shutdown, which would be caused by the liquid phase's eliminating or its introducing into the discharge line, will not be occurred, whereby the productivity is improved and stable continuous operation can be carried out.

The internal part of the reactor is divided into two phases: super critical monatomic alcohol phase, into which the reaction products are dissolved, and not-yet-decomposed polyester phase. The present inventors found that the temperature of the super critical monatomic alcohol phase is lower than that of the not-yet-decomposed polyester phase, particularly that, when the super critical monatomic alcohol is methanol, the temperature of super critical methanol phase is lower than that of not-yet-decomposed polyester phase by about 20° C.

That is to say, it is found that, in order to determine the boundary position formed between these two phases by utilizing such temperature difference, the temperature of each phase should be known. Therefore, by detecting the temperature of each phase with the temperature sensor equipped in the reactor, the boundary (interface) position formed between the super critical monatomic alcohol phase and aromatic polyester phase can be determined. Since it is impossible to use a common level meter due to the severe reaction conditions of high temperature and high pressure, it is only way for determining the boundary position to detect the temperature of each phase with the temperature sensor such as a thermocouple.

In discharging the above reaction products, the pressure in the above reactor can be reduced and, if required, can be reduced so as to reach the atmospheric.

Actually, when each spent PET bottle is recycled for the reuse of resources, metal, ash, resin other than PET, adhesive for attaching labels to the bottle, the labels, and the like, all of which are contained in the PET bottle, must be removed. Then, in order to improve the purity of each monomer component, which is recovered as the product, several treatments are required prior to the reaction step. For example, sorting of different kinds of resins other than the PET, detaching the labels, removing a cap, washing with detergent, ultrasonic cleaning and air separation must be carried out. It is extremely troublesome to perform such pre-treatments. Moreover, these pre-treatments downgrade the productivity and increase the recycle cost.

For overcoming this problem, in discharging of the reaction products from the reactor, aromatic divalent carboxylic acid ester and monatomic alcohol may be discharged continuously while the alcohol is saturated with this ester. Precisely, in a preferred embodiment, the amount of communicated methanol is determined so that the reaction products; aromatic divalent dimethyl carboxylate (dimethyl terephthalate) and diatomic alcohol (ethylene glycol) are discharged continuously together with the methanol, while the methanol is saturated with all amount of produced dimethyl terephthalate. Residue condensed in the above reactor can be intermittently discharged out of this process system through a discharge line from the bottom of the above reactor.

According to this embodiment, spent PET bottles, which have been collected and crushed, can be directly used as the material of this process. That it to say, the collected PET bottles, to each of which the metal, ash, resins other than PET, adhesive for the labels, labels, and the like are contained, can be used as the material as they are without the pre-treatments such as finely sorting, washing, and the like.

The discharged reaction products are introduced into a column in which the temperature is lower than that in the reactor, a column in which the pressure is lower than that in the reactor, or a column in which the temperature and pressure are lower than those in the reactor respectively. Then, oligomer components precipitated in the column can be recycled to the reactor. Thus, only monomer components can be directed to a purification step located on the downstream of the column, which ensures to obtain the highly purified monomer components.

In order to cool the above discharged products for the crystallization of the aromatic divalent carboxylic acid ester therefrom, heat exchange may be carried out between the reaction products and the above monatomic alcohol to be fed into the above reactor. Then, the above monatomic alcohol is heated while the above reaction products are cooled. Owing to this heat exchange between the discharged reaction products and monatomic alcohol to be fed into the reactor, energy cost can be saved,

DESCRIPTION OF THE PREFERRED EMBODIMENT

Now, the present invention is described more closely, referring to the preferred embodiments of the present invention shown in the accompanying drawings.

<The First Embodiment>

Figure 1:
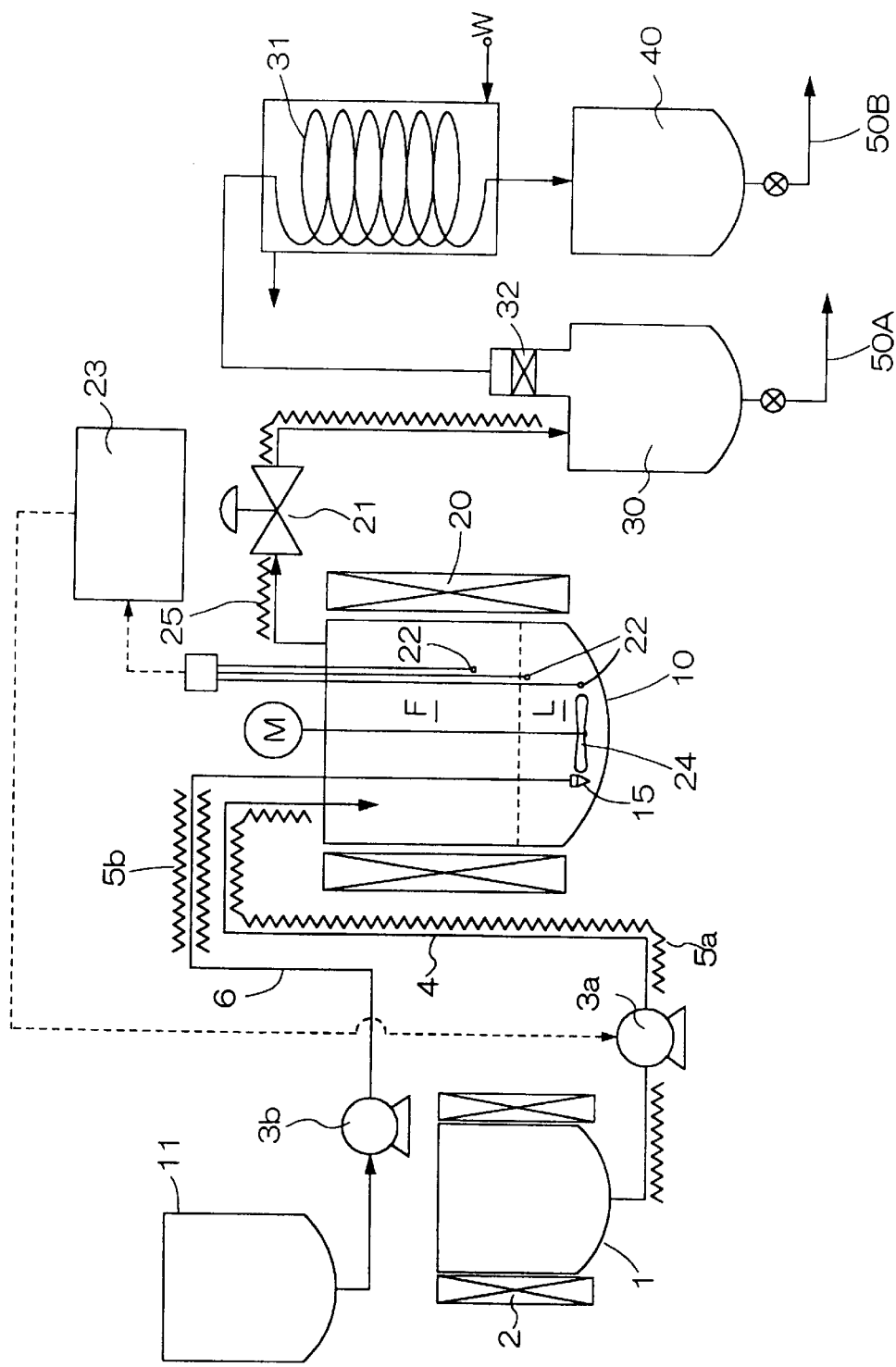
FIG. 1 is the flow diagram of the first embodiment according to the present invention.

FIG. 1 illustrates schematically the process flow diagram of the process for producing monomer components in the first embodiment of the present invention. The collected PET material (e.g., PET bottle) is sorted and washed so as to be crushed and the resultant material is fed to the melting tank 1 where the material is melted by heating the tank 1 with the heaters 2, 2. The melted aromatic polyester is fed continuously into the reactor 10 through the means of the metering pump 3a consisting a gear pump or the like. In this connection, the aromatic polyester feed line 4 is preferably provided with the heating means or hot insulation means 5a such as a heat insulating equipment.

Methanol consisting the monatomic alcohol of the present invention is fed from the methanol tank 11 via the methanol feed line 6 through the means of the metering pump 3b, into the reactor 10 by means of the nozzle 15, which is inserted in the reactor 10 so as to reach its bottom. In this case, the methanol is preferably fed with the constant flow rate. The methanol feed line 6 may be also provided with the heating means 5b or hot insulation means.

The reactor 10 is a pressure reactor, which can be proof against the super critical conditions of methanol (high temperature and high pressure). The reactor 10 is provided with the heaters 20, 20, by which the temperature in the reactor 10 is raised to the temperature being the same as or higher than the super critical temperature of methanol. This temperature in the reactor 10 is 512.6 to 673 K, which is the super critical condition of methanol, and is preferably 523 to 653 K. The pressure in the reactor 10 is controlled so as to be 3 to 30 MPa and be preferably 5 to 25 MPa. On the other hand, when ethanol is used as the monatomic alcohol, the temperature in the reactor is 513.9 to 673 K, which is the super critical condition of ethanol, and is preferably 523 to 653 K. The pressure in the reactor 10 is controlled so as to be 3 to 20 MPa and be preferably 5 to 15 MPa. The pressure control valve 21 controls the pressure in the reactor 10.

In the first embodiment, the aromatic polyester and monatomic alcohol are reacted in the reactor 10 in the weight proportion of 2 mol, preferably equal to or higher than 4 mol of monatomic alcohol per 1 mol of aromatic divalent carboxylic acid in the aromatic polyester.

The aromatic polyester and super critical methanol are reacted in the reactor 10 while they are stirred with the stirrer 24 so that the aromatic divalent dimethyl carboxylate and diatomic alcohol can be produced. As stated before, the temperature in the super critical methanol phase F is lower than the temperature of not-yet-decomposed polyester phase L by about 20° C. Then, the temperature difference between the two phases is detected by means of the temperature sensors 22, 22 . . . , which are located in the reactor 10 at many levels on its height direction, whereby a boundary position formed between these two phases can be detected by means of the controller 23. Then, on the basis of the result of this detection, the flow rate of the fed aromatic polyester into the reactor 10 is controlled by, for example, rotating speed of the metering pump 3b. Thus, by utilizing the detected temperature in the super critical methanol phase F, the boundary position (interface position) formed between the methanol phase F and the not-yet-decomposed polyester phase L can be controlled.

During the progress of the reaction, the resultant products are dissolved into the super critical methanol phase F. Then, the resultant products together with the super critical methanol, into which the products are dissolved, are introduced to the flash tank 30, via the discharge line 25, which is connected from the super critical methanol phase F, through the means of the pressure control valve 21. On the other hand, the decreased amount of aromatic polyester, which is caused by decomposition and by discharge, is compensated by the aromatic polyester added by means of the metering pump 3a, whereby the boundary position formed between the two phases is kept at the same level.

Since the reaction between the aromatic polyester and monatomic alcohol is one of typical ester exchange reactions, the components are allowed to come to certain equilibrium under the conditions of certain temperature and certain pressure. However, during the discharge of the reaction products together with the methanol, the equilibrium is shifted to the side of reaction products so that the decomposing reaction can be accelerated.

The reaction products and super critical methanol are introduced, through the discharge line 25, to the flash tank 30 where they are condensed. An extra vapor content, which can not be condensed in the flash tank 30, is liquefied by cooling water W communicated through the cooling coil 31 and is recovered in the methanol recovery tank 40. Solid particles of aromatic divalent dimethyl carboxylate as the reaction products are suspended in the above flash tank 30. If these solid particles were directly moved into the cooling coil 31, the coil 31 would be blocked. Accordingly, it is preferable that the filter 32 is provided between the flash tank 30 and cooling coil 31 so as to remove the solid particles.

A condensate liquid obtained by condensation in the flash tank 30 and a condensate liquid obtained in the methanol recovery tank 40 are, via the recovery line 50A and 50B respectively, transferred to a following separation step. In this separation step, the aromatic divalent dimethyl carboxylate and diatomic alcohol are separated from the reaction products, by means of e.g., distillation or crystallization. Then, the aromatic divalent dimethyl carboxylate and diatomic alcohol are recovered.

At the terminal stage of this process, the decomposed products, aromatic divalent dimethyl carboxylate and diatomic alcohol, which have been remained in the reactor 10, are required to be recovered with high yield. Therefore, intermittently or every predetermined hours, the pressure control valve 21 is opened so as to reduce the pressure in the reactor 10 to the atmospheric pressure for the discharge and recovery of the reaction products.

<The Second Embodiment>

In the above first embodiment, it is often required to carry out the sorting treatment and washing treatment (washing with detergent, ultrasonic cleaning, or the like) for the collected PET material (such as PET bottles). On the other hand, in the second embodiment, as stated below, the collected PET material are crushed as it is and the resultant crushed material can be directly subjected to a decomposing reaction. The crushed PET is heated and melted in the melting tank 1 provided with the heater 2. Then, the crushed PET is fed, via the aromatic polyester feed line 4, into the reactor 10 by means of the metering pump 3a.

On the other hand, methanol is derived from the methanol tank 11 by means of the methanol feed pump 3b and passed through the methanol feed line 6. Then, at the heat exchanger 7 on the way, heat exchange is carried out between the methanol and the discharged reaction products so that the temperature of methanol is increased to the reaction temperature. Next, the heated methanol is introduced into the reactor 10 by means of the nozzle 15, which is inserted in the reactor 10 so as to reach its bottom. Thus, the methanol is always communicated through in this process.

In the second embodiment, in the same manner as the first embodiment, the temperature in the reactor 10 is equal to or higher than the critical temperature of methanol, that is 512.6 to 673 K, and is preferably 523 to 653 K The pressure in the reactor 10 is controlled so as to be 3 to 30 MPa and be preferably 5 to 25 MPa by means of the pressure control valve 21. By the reaction performed between the aromatic polyester and super critical methanol, the aromatic divalent dimethyl carboxylate and diatomic alcohol are produced.

In the second embodiment, the reaction materials (aromatic polyester and methanol) in the reactor 10 are reacted in the different weight proportion from that of the first embodiment. Precisely, in the second embodiment, the weight proportion is equal to or higher than 10 mol, preferably equal to or higher than 40 mol of methanol per 1 mol of aromatic divalent carboxylic acid in the aromatic polyester. From the point of equivalency, the weight proportion should be 2 mol of methanol per 1 mol of acid. However, for the smooth discharge of the reaction products out of this process system, the methanol is preferably fed to the reactor in considerably excess of the equivalency. When the weight proportion is equal to or higher than 40 mol of methanol per 1 mol of aromatic divalent carboxylic acid in the aromatic polyester, the almost all amount of reaction products can be discharged in the form of being dissolved into the methanol.

During the progress of reaction, the decomposed products are formed and dissolved in the super critical methanol phase. The dissolved products are introduced from the methanol phase, via the discharge line 25, which is connected from the super critical phase in the upper portion of the reactor 10, to the oligomer separator 26, which comprises a packed tower, tower having no packing, or the like.

The oligomer components are separated in the oligomer separator 26 where the temperature is lower than that in the reactor 10 by 5 to 100° C. and preferably by 10 to 40° C.; the pressure is lower than that in the reactor 10 by 0.1 to 4 MPa and preferably by 0.2 to 2 MPa; or the temperature and pressure are lower than those in the reactor by the above mentioned differences respectively. After the pressure of precipitated oligomer components is increased, these components are returned, via the backing line 28 to the reactor 10 by means of the backing pump 27. Thus, only monomer components can be obtained from the oligomer separator 26, and introduced, via the heat exchanger 7 and pressure control valve 29, to the flash tank 30 located at the down stream.

The decreased amount of aromatic polyester, which is caused by decomposition, is compensated by the aromatic polyester added by means of the metering pump 3a, whereby the level of aromatic polyester can be kept to be constant. Metal, ash, resin other than PET, adhesive for attaching labels to the bottle, the labels, and the like, are contained in the aromatic polyester as the material. During progress of the reaction, the content proportions of the metal, ash and other impurities in the aromatic polyester phase are increased so that the impurities are enriched in the discharged reaction products. Accordingly, in order to keep the purity of product, it is preferable that the enriched residue such as the metal, ash, and the other impurities contained in the reactor 10 are discharged.

As stated before, the reaction between the aromatic polyester and monatomic alcohol is one of typical ester exchange reactions, the components are allowed to come to certain equilibrium under the conditions of certain temperature and certain pressure. However, during the discharge of the reaction products together with the methanol, the equilibrium is shifted to the side of reaction products so that the decomposing reaction can be accelerated.

In the second embodiment, when a lot of methanol is used, the amount of discharged aromatic divalent dimethyl carboxylate is increased. In this case, however, the temperature of the methanol rises, which increases the energy cost. Accordingly, it is preferable that at the down stream of the oligomer separator 26, heat exchange is carried out between the reaction products from the oligomer separator 26 and the methanol to be fed to the reactor 10. After the heat exchange, the reaction products are introduced to the flash tank 30 so as to be condensed. An extra vapor content, which can not be condensed, is passed through the filter 32 so that suspended solid particles of the reaction products are removed, and is liquefied by means of the cooling coil 31 before the recovery in the methanol recovery tank 40.

The reaction products are recovered in the flash tank 30 so that the aromatic divalent dimethyl carboxylate and diatomic alcohol can be recovered with large concentration by means of separating operation (not shown) such as distillation, crystallization, or the like. On the other hand, the methanol recovered in the methanol recovery tank 40 is returned, via the backing line 41, to the reactor 40.

Now, the effect of the present invention will be explained more closely on the basis of the following examples and comparative examples.

EXAMPLE 1

According to the First Embodiment

In the configuration shown in FIG. 1, an autoclave having the content volume of 5 lit. was used as the reactor (autoclave) 10. Then, the temperature in the reactor was set to be 603 K. First, 1000 g of melted PET was fed into the reactor and methanol was continuously fed to the autoclave with the flow rate of 1000 g/hr. During this operation, the reaction products were continuously discharged together with super critical methanol from the super critical methanol phase located in the upper portion of the reactor 10.

The boundary position (interface position) formed between the two phases was detected from the indicated values determined on the basis of temperatures measured by three thermocouples located at the lower level, middle level, and upper level, respectively in the reactor 10. For example, when the temperature in the lower PET liquid phase was 330° C., the temperature in the upper super critical methanol phase should be 310° C. Accordingly, the amount of fed PET is controlled so that the temperature adjacent to the interface position was 310 to 330° C. Thus, the boundary position between the phases could be kept to be at the same level.

Under these conditions, reaction was performed for 30 minutes while the reaction products were discharged together with the methanol. After this reaction, the pressure in the reactor 10 was reduced so as to reach the atmospheric pressure and the reaction products were discharged. The reaction products, which were discharged together with the methanol during reaction, and the reaction products, which were discharged after the reaction, were soluble into diethyl ether, which ensures that these two kinds of reaction products did not contain any not-yet-reacted PET.

The above reaction products were classified into a solid product, ethylene glycol, and methanol by means of filtering and distillation. Then, the dimethyl terephthalate was quantitatively determined as the monomer component with a gas chromatography. As shown in Table 1, 153 g of solid product was recovered during the reaction and its monomer purity was 95%. After the reaction, the pressure in the reactor 10 was decreased and 534 g of solid product could be additionally recovered and its monomer purity was 76%.

TABLE 1

Continuous Type (methanol was fed with the flow rate of 1000 g/hr)

| discharge | reaction temperature °C. | reaction pressure MPa | reaction time min. | amount of fed PET g | amount of recovered product g | monomer purity % |
|---|---|---|---|---|---|---|
| during reaction | 330 | 8.1 | 30 | 1000 | 153 | 95 |
| after reaction | 330 | 8.1 | 30 | 1000 | 534 | 76 |
| total | — | — | — | — | 687 | — |

After the reaction, the pressure in the reactor 10 was reduced and the reaction products were discharged for recovery, and the discharge operation was performed while the pressure in the reactor 10 was intermittently reduced to the atmospheric pressure. Thus, the total amount of recovered solid product was increased to 687 g. Then, the amount of monomer components contained in the residue in the reactor 10 was very small of 40 g. Additionally, deterioration such as carbonization was not occurred in the solid product. Therefore, the decomposition reaction could continue by adding the PET and methanol.

EXAMPLE 2
According to the First Embodiment

The reaction was carried out in the same way as Example 1 except that ethanol was used as the monatomic alcohol in stead of the methanol and except that the pressure in the reactor (autoclave) 10 was 8.0 MPa.

The above reaction products were classified into a solid product, ethylene glycol, and ethanol by means of filtering and distillation. Then, dimethyl terephthalate was quantitatively determined as the monomer component with a gas chromatography.

The results are shown in Table 2.

TABLE 2

Continuous Type (ethanol was fed with the rate of flow of 1000 g/hr)

| discharge | reaction temperature °C. | reaction pressure MPa | reaction time min. | amount of fed PET g | amount of recovered product g | monomer purity % |
|---|---|---|---|---|---|---|
| during reaction | 330 | 8.0 | 30 | 1000 | 145 | 91 |
| after reaction | 330 | 8.0 | 30 | 1000 | 508 | 73 |
| total | — | — | — | — | 653 | — |

As shown in Table 2, 145 g of solid product was recovered during the reaction and its monomer purity was 91%. After the reaction, the pressure in the reactor 10 was reduced and 508 g of solid product could be recovered again and its monomer purity is 73%.

Comparative Example 1

For comparison with Examples 1 and 2, experiments were performed with known batch type reactions. In each experiment, first, 50 to 1000 g of PET and 650 to 700 g of methanol were fed into the reactor (autoclave) having the content volume of 5 lit. Then, the reactions were carried out at the reaction temperature of 300 to 330° C. and the pressure of 8.1 MPa for the reaction time of 15 to 120 minutes. After each reaction, the reactor 10 was cooled and opened so as to recover the reaction products.

In each experiment, the amount of recovered reaction products was measured. Then, the effects of variation in reaction time on the amount of recovered products and on the monomer purity were checked. Further, the effect of variation in amount of fed PET and the effect of variation in reaction temperature on the amount of recovered products were also checked. The results are shown in Table 3.

TABLE 3

Batch Type (amount of fed methanol was 650 to 700 g)

| Experiment No. | reaction temperature °C. | reaction pressure MPa | reaction time min. | amount of fed PET g | amount of recovered product g | monomer purity % |
|---|---|---|---|---|---|---|
| 1 | 300 | 8.1 | 15 | 500 | 48 | 9 |
| 2 | 300 | 8.1 | 30 | 500 | 161 | 51 |
| 3 | 300 | 8.1 | 60 | 500 | 252 | 49 |
| 4 | 300 | 8.1 | 120 | 500 | 208 | 50 |
| 5 | 300 | 8.1 | 30 | 1000 | 168 | 37 |
| 6 | 330 | 8.1 | 30 | 500 | 266 | 46 |

As shown in Table 3, by the increase of reaction time, once it exceeded 30 minutes, the amount of recovered products and monomer purity were not improved greatly. Further, both of variation in amount of fed PET and variation in reaction temperature did not give large effect on the amount of recovered products.

Comparing with the continuous type in Example 1, in each experiment, the amount of recovered product was decreased by about or more than 50%, and its monomer purity was decreased by about or more than 25%. Additionally, it took few hours to increase the temperature so as to reach the reaction temperature and it took also few hours to cool the reactor 10 for opening the reactor. Therefore, in this comparative example, the PET decomposing process was carried out with extremely low efficiency.

Reference Example 1

In the configuration shown in FIG. 1, an autoclave having the content volume of 5 lit. was used as the reactor (autoclave). Then, the temperature in the autoclave was set to be 603 K. First, 1000 g of melted PET was fed into the autoclave. Then, methanol was continuously fed to the autoclave with the flow rate of 1000 g/hr. During this operation, the reaction products were continuously discharged together with the super critical methanol from the upper portion of reactor 10 so that the pressure in the reactor 10 is 4.0 MPa.

The reaction was carried out for 30 minutes in the same manner as Example 1. Then, after the reaction, the pressure in the reactor 10 was reduced so as to reach the atmospheric pressure for the discharge of reaction products. The results are shown in Table 4.

TABLE 4

Continuous Type (methanol was fed with the flow rate of 1000 g/hr)

| discharge | reaction temperature ° C. | reaction pressure MPa | reaction time min. | amount of fed PET g | amount of recovered product g | monomer purity % |
|---|---|---|---|---|---|---|
| during reaction | 330 | 4.0 | 30 | 1000 | 224 | 73 |
| after reaction | 330 | 4.0 | 30 | 1000 | 314 | 78 |
| total | — | — | — | — | 538 | — |

As shown in Table 4, 224 g of products was recovered during the reaction and its monomer purity is 73%, and after the reaction, 314 g of products was recovered and its monomer purity was 78%. Comparing with Example 1, the total amount 538 g of recovered products was smaller than that of Example 1 by 149 g, further, the monomer purity of the recovered solid products was decreased by about 22%. According to this reference example, it was ensured that such decrease was caused by the low pressure of 4.0 MPa in the reactor 10.

Reference Example 2

The reaction was performed in the configuration shown in FIG. 1, but in this reference example, any temperature detecting means is not provided. An autoclave having the content volume of 5 lit. was used as the reactor (autoclave) 10. First, 1600 g of PET was fed into the reactor. Then, methanol was continuously fed into the autoclave with the flow rate of 1000 g/hr. During this operation, the super critical methanol and decomposed product were continuously discharged from the upper portion of the reactor 10. When about 30 minutes passed since the reaction was started, not-yet-reacted PET was attached and accumulated on the internal surface of the upper flange (cover) of the reactor 10 so that the stirrer could not rotate, whereby the operation could not continue.

EXAMPLE 3

Figure 2:
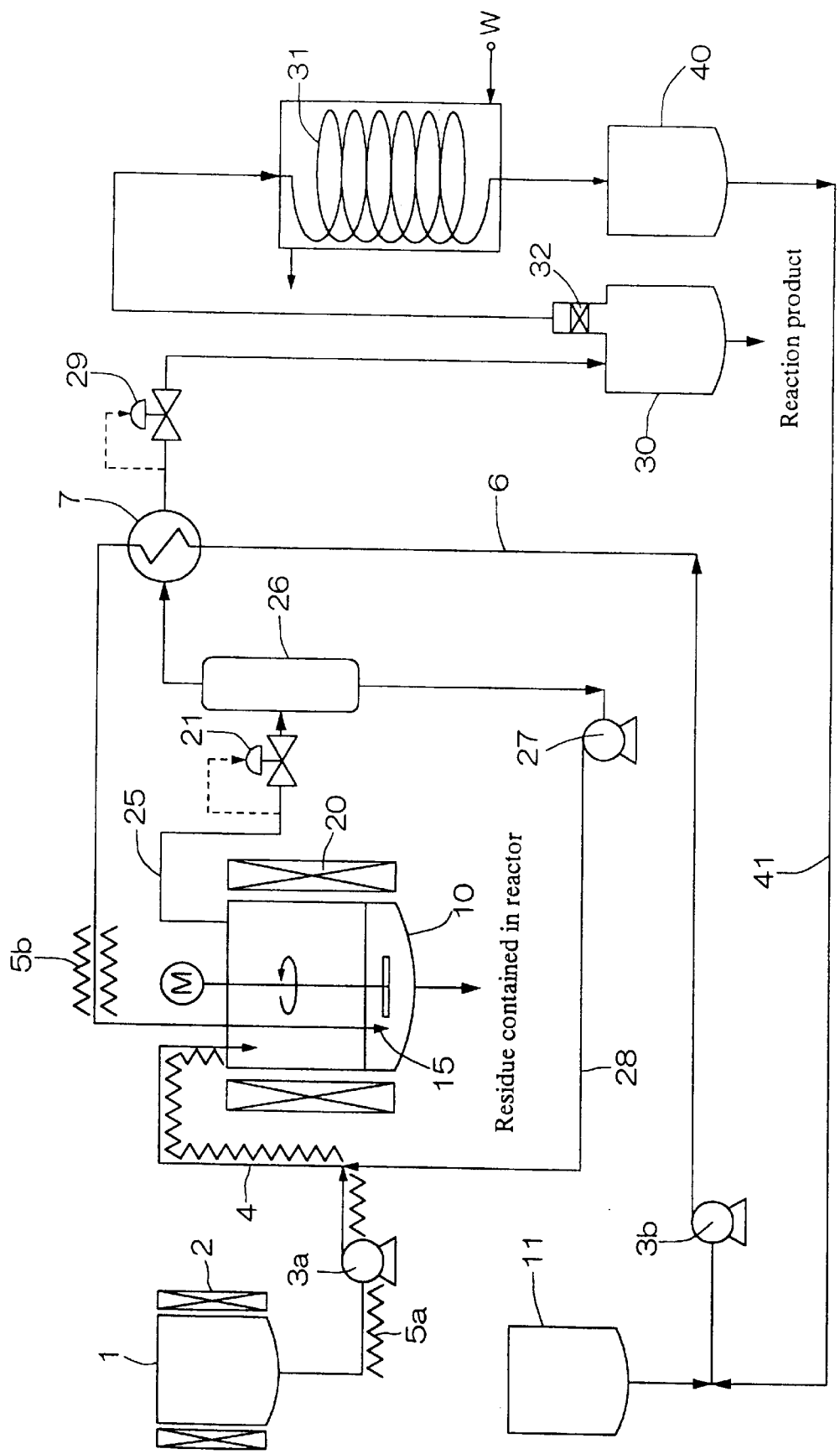
FIG. 2 is the flow diagram of the second embodiment according to the present invention.

In the configuration shown in FIG. 2, an autoclave having the content volume of 5 lit. was used as the reactor (autoclave) 10. The temperature in this autoclave was set to be 603 K First, 1000 g of collected PET flakes, which included 10 ppm of ash and 60 ppm of label material, was melted and fed into the reactor. Then, methanol was fed continuously to the reactor. During this operation, the pressure in the reactor 10 was reduced to 8.1 MPa, and the discharge from the methanol phase located at the upper portion of the reactor 10 was performed continuously.

PET was always fed into the reactor 10 so that the level of the PET phase could be kept to be constant. Further, every 24 hours, PET and impurities contained in the reactor 10 were discharged, via the discharge line from the bottom of the reactor, so as to prevent impurities from contaminating into the discharged decomposed product. The reaction products discharged from the reactor 10 were introduced into the oligomer separator 26 which was kept to be at the temperature of 573 K and at the pressure of 7.0 MPa. In the separator 26, the oligomer components were precipitated and separated from the introduced reaction products, and were recovered from the bottom of the separator for recycling to the reactor 10.

On the other hand, the reaction products were discharged from the oligomer separator 26. Next, heat exchange was carried out at the heat exchanger 7 between the reaction products and the methanol to be fed. After that, the reaction products were recovered in the flash tank 30. 42 mol of methanol was communicated per 1 mol of decomposed product (dimethyl terephthalate). The reaction products recovered from the flash tank 30 were separated and refined by this communicated methanol. Thus, 1270 g of dimethyl terephthalate and 406 g of ethylene glycol were obtained per 1 hour. According to the analysis of this dimethyl terephthalate, purity was equal to or more than 99% and the ash content was equal to or smaller than 1 ppm.

Comparative Example 2

An autoclave having the content volume of 5 lit. was used as the reactor (autoclave) 10. The temperature in this autoclave was set to be 603 K. The collected PET flakes being similar to that of Example 3 were used as the material. That is to say, the material contained 10 ppm of ash and 60 ppm of label material. First, 1000 g of collected PET flakes were melted and fed into the reactor. Then, methanol was fed continuously into the reactor. During this operation, the pressure in the reactor 10 was reduced to 8.1 MPa, and the continuous discharge operation from the methanol phase located at the upper portion of the reactor 10 was performed.

PET was always fed into the reactor 10 so that the level of the PET phase could be kept to be constant. The reaction products, which had been discharged from the reactor 10, were recovered in the flash tank. 10 mol of methanol was communicated per 1 mol of decomposed product (dimethyl terephthalate). The reaction products recovered from the flash tank 30 were separated and refined by this communicated methanol. Thus, 306 g of dimethyl terephthalate and 98 g of ethylene glycol were obtained per 1 hour. According to the analysis of this dimethyl terephthalate, the oligomer components were contained and its monomer purity was 95 % and the ash content was 40 ppm. Additionally, in this comparative example, the temperature of the methanol to be fed to the reactor 10 was risen. Hence, the power consumption was increased so as to be larger by 20% than that of the case where heat exchange was carried out.

As stated above, according to the present invention, the recovery, separation, and the like of monomer components can be simply carried out under industrially advantageous conditions, and the monomer components can be continuously produced from aromatic polyester with high efficiency.

What is claimed is:

1. A process for continuously producing monomeric components of an aromatic polyester by reaction of said aromatic polyester and a super critical monohydric alcohol to obtain an aromatic dicarboxylic acid ester and dihydric alcohol, said process comprising the steps of:
   continuously feeding said aromatic polyester and said monohydric alcohol into a reactor while said reactor is maintained under a super critical condition of said monohydric alcohol;
   reacting said aromatic polyester and said super critical monohydric alcohol and continuously discharging from said reactor the resultant reaction products comprising said aromatic dicarboxylic acid ester and said dihydric alcohol, together with said monohydric alcohol; and
   separating, from said discharged resultant products, said aromatic dicarboxylic acid ester and said dihydric alcohol, thereby recovering said aromatic dicarboxylic acid ester and said dihydric alcohol;

wherein said reactor is maintained at a temperature of from about 512.6 to about 673° K and a pressure of from about 3 to about 30 MPa and said monohydric alcohol is fed into said reactor at a constant flow rate, and the flow rate of said aromatic polyester fed into said reactor is controlled based upon a determination of the position of a boundary formed between a phase of said super critical monohydric alcohol and a phase of said aromatic polyester.

2. A process for continuously producing monomeric components according to claim 1, wherein temperature sensors are provided in said reactor for measuring the temperature of said phase of said super critical monohydric alcohol and the temperature of said phase of said aromatic polyester, and said position of said boundary formed between said phase of said super critical monohydric alcohol and said phase of said aromatic polyester is determined based on the measured temperatures.

3. A process for continuously producing monomeric components according to claim 1, wherein the pressure in said reactor is decreased after an interval and said reaction products are discharged therefrom.

4. A process for continuously producing monomeric components of an aromatic polyester by reaction of said aromatic polyester and a super critical monohydric alcohol to obtain an aromatic dicarboxylic acid ester and a dihydric alcohol, said process comprising the steps of:

continuously feeding said aromatic polyester and said monohydric alcohol into a reactor while said reactor is maintained under a super critical condition of said monohydric alcohol;

reacting said aromatic polyester and said super critical monohydric alcohol and continuously discharging from said reactor the resultant reaction products comprising said aromatic dicarboxylic acid ester and said dihydric alcohol, together with said monohydric alcohol; and separating, from said discharged resultant products, said aromatic dicarboxylic acid ester and said dihydric alcohol, thereby recovering said aromatic dicarboxylic acid ester and said dihydric alcohol;

wherein said reactor is maintained at a temperature of from about 512.6 to 673 °K and a pressure of from about 3 to about 30 MPa and said reaction products are continuously discharged from said reactor with said aromatic dicarboxylic acid ester being dissolved in and saturated with said monohydric alcohol.

5. A process for continuously producing monomeric components according to claim 4, wherein said reaction products which are continuously discharged from said reactor are introduced into an oligomer separator, in which the temperature, pressure, or both temperature and pressure is lower than that in said reactor, and precipitated oligomeric components are returned to said reactor from said oligomer separator.

6. A process for continuously producing monomeric components according to claim 4, wherein, in order to cool and thereby crystallize out said aromatic dicarboxylic acid ester from said reaction products, heat exchange is carried out between said reaction products and said monohydric alcohol fed to said reactor so that said monohydric alcohol is heated and said reaction products are cooled.

7. A process for continuously producing monomeric components according to claim 4, wherein enriched residue from said reactor is intermittently discharged via a discharge line from a lower portion of said reactor.

8. A process for continuously producing monomeric components according to claim 4, wherein said aromatic polyester fed to said reactor is obtained from used PET bottles, each of which was collected and crushed and wherein the resultant crushed material is used substantially as is.

* * * * *